United States Patent [19]
Sedlak et al.

[11] Patent Number: 5,194,666
[45] Date of Patent: Mar. 16, 1993

[54] PROCESS FOR PREPARING ESTERS OF 3,5,6-TRICHLOROSALICYCLIC ACID

[75] Inventors: John A. Sedlak, Stamford; Mark A. Higgins, New Haven; Amy P. Essenfeld, Stamford, all of Conn.

[73] Assignee: American Cyanamid Company, Stamford, Conn.

[21] Appl. No.: 921,785

[22] Filed: Jul. 30, 1992

[51] Int. Cl.$^5$ .............................................. C07C 69/76
[52] U.S. Cl. ....................................... 560/62; 562/474
[58] Field of Search ........................... 560/62; 562/474

[56] References Cited

U.S. PATENT DOCUMENTS

| | | | |
|---|---|---|---|
| 3,062,877 | 11/1962 | Hanna | 560/65 |
| 3,597,362 | 8/1971 | Bollyky et al. | 252/186 |
| 3,749,679 | 7/1973 | Rauhut | 252/188.3 |
| 3,781,329 | 12/1973 | Bollyky | 260/479 S |
| 3,816,326 | 6/1974 | Bollyky | 252/188.3 |
| 4,308,395 | 12/1981 | Manfre et al. | 560/65 |

FOREIGN PATENT DOCUMENTS 2016582 10/1970 Fed. Rep. of Germany .
2-658192 8/1991 France .
3-197443 8/1991 Japan .

OTHER PUBLICATIONS

AG Leulier and Pinet, Bull. Soc. Chim, 41, 1362–1370 (1927).

*Primary Examiner*—Paul J. Killos
*Attorney, Agent, or Firm*—Frank M. Van Riet

[57] ABSTRACT

An improved process for the synthesis of esters of 3,5,6-trichlorosalicylic acid in quantitative yield comprises reacting the acid with an alcohol under distillation conditions in the presence of a titanium ester or chelate catalyst, whereby byproduct ether formation from the alcohol is suppressed. The process is especially applicable to a process by which salicylic acid is chlorinated first in concentrated sulfuric acid and then with iodine catalyst to make the trichlorosalicylic acid which is extracted and then reacted with an alcohol and a titanium catalyst to make the ester.

17 Claims, No Drawings

PROCESS FOR PREPARING ESTERS OF 3,5,6-TRICHLOROSALICYCLIC ACID

BACKGROUND OF THE INVENTION

The present invention relates to the production of intermediates to make agents useful for the production of light by chemiluminescence.

The use of 3,5,6-trichlorosalicylic acid as an intermediate in the preparation of n-pentyl 3,5,6-trichlorosalicylate was described by Rauhut in Example XXVI of U.S. Pat. No. 3,749,679. The latter compound is an intermediate in the preparation of bis(2,4,5-trichloro-6-carbopentoxyphenyl)oxalate which is useful in chemiluminescent compositions, as described in U.S. Pat. Nos. 3,597,362; 3,781,329; and 3,816,326.

Rauhut also discloses in Example XXVI of U.S. Pat. No. 3,749,679 the conversion of 3,5,6-trichlorosalicylic acid to the n-pentyl ester by refluxing it in n-pentyl alcohol containing a catalytic amount of sulfuric acid. The crude product is obtained in a yield of about 73% of theoretical. The combination of Hanna, U.S. Pat. No. 3,062,877, Leulier and Pinet, *Bull. Soc. Chim.* 41, 1362–1370 (1927), and Rauhut indicates an overall yield for the preparation of the n-pentyl ester, starting with salicylic acid and chlorinating, of about 53% of theoretical.

Manfre, Mohan and Rauhut disclose in U.S. Pat. No. 4,308,395 processes that produce significantly higher yields of 3,5,6-trichlorosalicylic acid and esters thereof, starting with salicylic acid. In accordance with that invention, salicylic acid is treated with gaseous chlorine in concentrated sulfuric acid to form 3,5-dichlorosalicylic acid. This product is converted by further chlorination in oleum, containing iodine, at about 40°–60° C., to 3,5,6-trichlorosalicylic acid, which is recovered by drowning the reaction mixture in ice and water, whereupon the product precipitates as a solid. The 3,5,6-trichlorosalicylic acid precipitate can be extracted from the drowned reaction mixture by mixing in a water-immiscible aromatic hydrocarbon solvent at a temperature of at least 60° C., and separating the organic phase, which contains the 3,5,6-trichlorosalicylic acid. Xylene is a preferred immiscible solvent for this purpose. The process is also applicable in the preparation of esters of 3,5,6-trichlorosalicylic acid represented by formula (I)

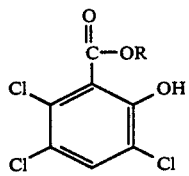

(I)

in which R represents alkyl ($C_3$–$C_{20}$). A solution of 3,5,6-trichlorosalicylic acid is prepared as described above, by extracting the drowned reaction mixture with a mixture of water-immiscible aromatic hydrocarbon solvent and an alcohol ($C_3$–$C_{20}$). This mixture is treated with a catalytic amount of a strong acid, such as sulfuric acid, p-toluenesulfonic acid, and the like, and heated at an elevated temperature to evaporate the water-alcohol azeotrope from the solution which contains the compound of formula (I), in the immiscible organic solvent.

In one especially preferred embodiment, the water-immiscible hydrocarbon solvent is xylene, the extraction is at 75°–100° C., the alcohol is n-pentanol, and the acid catalyst is concentrated sulfuric acid.

In practice, it has been found that such a process has at least one drawback; namely, that a large amount of dipentyl ether is formed as a byproduct. The large excess of pentanol required decreases the product yield per batch.

It has now been discovered that titanium esters and chelates, used in place of acid catalysts, selectively catalyze esterification, to the virtual exclusion of etherification. Moreover, the loading of pentanol needed drops considerably. Finally, the process has been found to be broadly applicable to esterification of this acid with other alcohols, even if the technique of Manfre et al is not used.

Some advantages of the present invention are as follows:

1. The esters of 3,5,6-trichlorosalicylic acid are obtained in very high purity, and in a relatively high yield.

2. The esters of 3,5,6-trichlorosalicylic acid can be prepared directly from salicylic acid by a series of steps which can all be performed in a single reaction vessel.

3. The esters of 3,5,6-trichlorosalicylic acid can also be obtained in a very high yield and purity, without the need for isolating the 3,5,6-trichlorosalicylic acid. The overall yield from salicylic acid to n-pentyl 3,5,6-trichlorosalicylate is excellent and the purity of the product is higher than about 98%.

4. The elimination of ether byproduct formation allows the reduction of the alcohol charge from 4 eq. to 1.75 eq. or less. Thus, a higher charge of the 3,5,6-trichlorosalicylic acid is allowed per campaign, and it is no longer necessary to remove and discard the byproduct as waste.

SUMMARY OF THE INVENTION

In accordance with the present invention, esters of 3,5,6-trichlorosalicylic acid represented by the formula

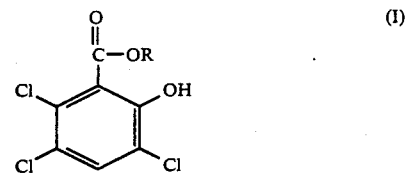

(I)

in which R represents alkyl ($C_1$–$C_{20}$) are prepared by a process comprising:

(1) preparing a reaction mixture comprising 3,5,6-trichlorosalicylic acid, a solvent, and, from about 100 mol % to about 175 mol %, based on said 3,5,6-trichlorosalicylic acid, of an alcohol having 1 to 20 carbon atoms, (2) adding a catalytic amount of a tetraalkyl titanate or a titanium chelate to the mixture of step (1) and, (4) heating the mixture and distilling until removal of water from the mixture is substantially complete, leaving a solution containing the compound of formula (I), trace amounts or less (as determined by HPLC) of byproduct ether of the formula $R_2O$, wherein R is as above defined, and tolerable amounts (as determined by HPLC) of unreacted 3,5,6-trichlorosalicylic acid.

When used herein, the term "HPLC" refers to that well-known analytical technique called high pressure liquid chromatography, a sensitive method to measure quantities of organic materials down to trace amounts and to determine the virtual absence of them.

In a stand-alone process, the 3,5,6-trichlorosalicylic acid made by methods described in the prior art may be converted into an ester of formula (I) by the process broadly outlined above and exemplified in detail hereinafter.

In a further process according to this invention the compound of formula (I) is made by steps comprising (1) contacting a solution of salicylic acid in concentrated sulfuric acid with chlorine at a temperature below 35° C. until essentially all of the salicylic acid is converted into monochlorosalicylic acid, further converting the monochlorosalicylic acid to 3,5-dichlorosalicylic acid by contacting it with chlorine at a temperature in the range 50°-75° C., (2) adding to the product solution of 3,5-dichlorosalicylic acid about 4 moles of sulfur trioxide for each mole of salicylic acid that was used in step (1), with the temperature of the solution at or below 55° C. during the addition of sulfur trioxide, (3) adding a catalytic amount of iodine to the solution obtained by step (2), (4) contacting the solution obtained in step (3) with gaseous chlorine while maintaining the solution temperature about 40°-60° C., until absorption of chlorine by the solution has ceased, (5) cooling the reaction mixture from step (4) to ambient temperature and adding the cooled reaction mixture to water at 0° C., thereby precipitating 3,5,6-trichlorosalicylic acid as a solid, (6) extracting the water containing precipitated 3,5,6-trichlorosalicylic acid with a water-immiscible solvent at a temperature of at least 60° C. to form a two-phase liquid mixture with the 3,5,6-trichlorosalicylic acid in the organic phase, (7) separating the organic phase from the aqueous phase, (8) removing water from the organic phase, if necessary, to less than 0.2 weight percent, (9) adding from about 100 mol % to about 175 mol %, based on said 3,5,6-trichlorosalicylic acid, of an alcohol having 1 to 20 carbon atoms,

(10) adding a catalytic amount of a tetraalkyl titanate or a titanium chelate to the separated organic phase, and,

(11) distilling the water azeotrope from the mixture leaving a solution containing the compound of formula (I), trace amounts or less (as determined by HPLC) of by-product ether of the formula $R_2O$, wherein R is as above defined, and tolerable amounts (as determined by HPLC) of unreacted 3,5,6-trichlorosalicylic acid.

In a preferred aspect of this embodiment, the gaseous chlorine is contacted with the solution of salicylic acid at a temperature of 5°-10° C., the 5-chlorosalicylic acid is converted to 3,5-dichlorosalicylic acid by contact with chlorine at 65°-70° C.; 100-150 milligrams of iodine per mole of the salicylic acid charged in step (1) is added in step (3), and gaseous chlorine is contacted with the reaction mixture at about 47°-54° C. in step (4).

In preferred aspects of the present processes, the alcohol used for the esterification contains 2-8 carbon atoms and the initial reaction mixture contains about 150 mol % of said alcohol, based on said 3,5,6-trichlorosalicylic acid; the alcohol comprises n-pentanol; the tetraalkyl titanate or titanium chelate is present in an amount of from about 1.5 to about 7.5 wt %, based on said 3,5,6-trichlorosalicylic acid, and is selected from (i) those of the formula $(R'O)_4Ti$, wherein the groups R' represent independently an alkyl group of from 2 to 10 carbon atoms; (ii) an acetonyl acetonate chelate of titanium; (iii) an ethyl acetoacetate titanium chelate; or (iv) a mixture of any of the foregoing; the titanium compound comprises from about 2.0 to about 5.0 wt %, and is selected from tetraisopropyl titanate, tetra-n-butyl titanate, titanium acetonyl acetonate chelate, titanium ethyl acetoacetate chelate, or a mixture of any of the foregoing; the solvent is a water-immiscible hydrocarbon and comprises a mixture of xylene isomers, toluene or a mixture of any of them; and the mixture prior to azeotropic distillation comprises about 4.0-7.0 parts by weight of a mixture of (i) toluene and xylenes or (ii) xylenes and about one part by weight of n-pentanol and the n-pentanol is present in an amount corresponding to about 150 mol % based on said 3,5,6-trichlorosalicylic acid

DETAILED DESCRIPTION OF THE INVENTION

In carrying out the preparation of esters of 3,5,6-trichlorosalicylic acid directly from the trichlorosalicylic acid, it is convenient to charge a vessel at room temperature with the acid, with the solvent and with the alcohol. Either water-miscible or water-immiscible solvents can be used. Water-miscible solvents should have a boiling point high enough to be capable of allowing the distilling out of the water of reaction as it forms. Azeotropic distillation, however, and water-immiscible solvents are preferred. The vessel will be fitted with a distillation system, such as a condenser and a Barrett trap, and a stirrer and a nitrogen purge will be used in common practice. Conventional heating means, such as an electric mantle will be used. The mixture will be stirred and heated to about 135°-140° C., whereupon the solution refluxes. After a period of time, e.g., 30 minutes, the lower portion of the trap contents is withdrawn generally removing less than one part of water. The catalyst, in the amount specified above and in the detailed examples, is then added in one portion and the stirred mixture is allowed to reflux while water is distilled, preferably azeotropically, into the trap. Depending on the catalyst and the amount, as will be seen later, the water will cease coming off after from about 6 to about 24 hours. Analysis of the solution at this point by high pressure liquid chromatography shows at most only a trace of ether byproduct, e.g., dipentyl ether if n-pentanol is used, and at most only a trace of unreacted 3,5,6-trichlorosalicylic acid.

In carrying out the preparation of esters of 3,5,6-trichlorosalicylic acid from salicylic acid, gaseous chlorine is passed into a vigorously stirred solution of salicylic acid in concentrated sulfuric acid, preferably 96-98% sulfuric acid, at a temperature below 35° C., preferably about 5°-10° C., until essentially all of the salicylic acid is converted to a monochlorosalicylic acid mixture. The mixture of 3-, and 5-chlorosalicylic acids is then further converted to 3,5-dichlorosalicylic acid by chlorination at a temperature of about 50°-75° C., preferably 65°-70° C. The stirring should be just vigorous enough to permit rapid reaction. Optionally, the chlorination may be carried out under pressure to increase the rate of reaction. Completion of the formation of the monochlorosalicylic acid and the 3,5-dichlorosalicylic acid may be determined by gas phase chromatography on samples of the reaction mixture. The in situ yield of 3,5-dichlorosalicyclic acid at this point is about 95-98% of theoretical.

In carrying out the conversion of the 3,5-dichlorosalicylic acid to 3,5,6-trichlorosalicylic acid, sulfur trioxide is added to the concentrated sulfuric acid to provide at least 4 moles of sulfur trioxide per mole of salicylic acid originally used. This is followed by the addition of a catalytic amount of iodine, about 20-500 milligrams, preferably about 100-150 milligrams, per mole of salicylic acid used. During the course of the addition of the sulfur trioxide, the temperature is prevented from exceeding 60° C. by external cooling, as necessary. Chlorine gas is then passed into the reaction mixture, at about 40°-60° C., until the uptake of chlorine ceases, as indicated by the initiation of bubbling at a gas bubbler device on the exhaust end of the reactor. The chlorination is carried out over about 0.5-2 hours, preferably about 0.5-0.75 hour. Again, the chlorination may optionally be carried out under pressure to increase the rate of reaction.

Upon completion of the chlorination, the reaction mixture is cooled to ambient conditions and then added to a mixture of ice and water to precipitate the 3,5,6-trichlorosalicylic acid as a solid. The solid may then be recovered by standard methods, such as filtration or centrifugation, washed with water and dried to obtain 3,5,6-trichlorosalicylic acid in a yield of about 78% of theoretical.

The alcohol having 1-20 carbon atoms may be added in admixture with the water-immiscible solvent only if the alcohol is substantially insoluble in water. Otherwise, the alcohol should be added in step (8), described above, i.e., any alcohol may be added in step (8), however, only substantially water-insoluble alcohols should be added in step (6) in conjunction with the solvent.

Preferably, the mixture of ice, water, and 3,5,6-trichlorosalicylic acid is stirred with a mixture of a water-immiscible solvent and a water-insoluble alcohol having 1 to 20 carbon atoms at a temperature of at least 60° C., preferably about 75°-100° C., to extract the 3,5,6-trichlorosalicylic acid into the organic phase.

In all aspects of the invention, suitable water-immiscible solvents include benzene, toluene, xylene, chlorobenzene, nitrobenzene, and the like. The preferred solvent is xylene, a mixture of o-, m-, and p-xylenes, alone, or in further combination with toluene. Suitable water-miscible solvents include dimethyl formamide, dimethyl sulfoxide, 1,2-diethoxyethane and the like. It is understood, however, that the water-miscible solvents are only used in the process where the starting material is 3,5,6-trichlorosalicylic acid.

Suitable alcohols include methanol, ethanol, n-propanol, n-butanol, n-pentanol, 2-ethylhexanol, dodecanol, octadecanol, eicosanol, and the like. The especially preferred alcohol is n-pentanol.

The two-phase liquid mixture is stirred for a period sufficient to extract essentially all of the 3,5,6-trichlorosalicylic acid into the organic phase and the mixture is allowed to settle. The organic phase is then separated from the aqueous phase and, if necessary, water is removed therefrom until less than about 0.2 weight percent remains, such as by azeotropic distillation or drying over a drying agent. Preferably, the aqueous phase is extracted again with a fresh mixture of solvent and alcohol. The organic phase is then separated from the aqueous phase and combined with the first organic extract after water is removed therefrom.

The organic extract, containing 3,5,6-trichlorosalicylic acid is treated with a catalytic amount of a titanium catalyst described above and heated at an elevated temperature, e.g., 135°-140° C., to azeotrope water therefrom and obtain a solution of the compound of formula (I).

Suitable titanium compounds which may be used are set forth above. The desired product can be recovered from the solution by stripping off the solvent and excess alcohol, and distilling the residue.

The following examples illustrate the present invention and are not meant to limit the invention except as set forth in the appended claims. All parts are by weight unless otherwise indicated.

EXAMPLE 1

Preparation of n-Pentyl 3,5,6-trichlorosalicylate

Into a suitable reaction vessel equipped with a mechanical stirrer, a condenser, a Barrett trap, and nitrogen purge are added 500 parts of 3,5,6-trichlorosalicylic acid (TCSA), 978 parts of xylenes, 308 parts of toluene, and 274 parts of n-pentanol. The ratio of hydrocarbon solvents to pentanol is 4.7 to 1. The slurry is agitated rapidly and 10 parts of titanium tetraisopropoxide is added as an esterification catalyst. The mixture is heated to reflux and the water of reaction (36 parts) is removed via the Barrett trap. When water is no longer collected in the Barrett trap, refluxing is discontinued. According to high pressure liquid chromatographic (HPLC) analysis, the reaction mixture contains 596 parts of n-pentyl 3,5,6-trichlorosalicylate (PTCSA), corresponding to 97.2% molar yield on real TCSA charged. No pentyl ether or unreacted TCSA is detected.

EXAMPLES 2-5

Preparation of n-Pentyl 3,5,6-trichlorosalicylate

Several different catalysts are used in the process of this invention and the results are compared.

The following general procedure is used: The reaction equipment is a suitable vessel fitted with a motorized stirrer, thermometer, and Barrett trap under a reflux condenser protected from atmospheric moisture with a drying tube. The flask is heated with an electric mantle.

To the vessel at room temperature are charged 50.0 parts of 3,5,6-trichlorosalicylic acid, 27.4 parts of n-pentanol, and 150 parts of mixed xylenes. The ratio of xylenes to pentanol is 5.47 to 1.

The stirred mixture is heated to 135°-140° C., where it is a refluxing solution. After one-half hour, the lower portion of the Barrett trap contents is withdrawn to remove less than one part of water. The catalyst, 2.5 parts, is then added in one portion and the stirred mixture is allowed to reflux while water distills into the Barrett trap.

The results of analyzing the products of four processes with titanium catalysts and two with acid and tin catalysts, respectively, for comparison purposes are set forth in the Table which follows:

TABLE

SYNTHESIS OF PENTYL 3,5,6-TRICHLOROSALICYLATE
Xylenes Solvent, Reaction Temp. 135-140° C.

| Ex. | Catalyst[1] | Excess pentanol[2] | Reaction Time hrs.[3] | H$_2$O distilled, % of theory | R$_2$O formed % |
|---|---|---|---|---|---|
| 2 | TPT[4] | 50 | 6¼ | 103 | Trace |
| 3 | TBT[5] | 50 | 6¾ | 97 | Trace |
| 4 | ATC[6] | 50 | 18 | 117 | Trace |
| 5 | EATC[7] | 50 | 21 | 114 | Trace |

TABLE-continued
SYNTHESIS OF PENTYL 3,5,6-TRICHLOROSALICYLATE
Xylenes Solvent, Reaction Temp. 135-140° C.

| Ex. | Catalyst[1] | Excess pentanol[2] | Reaction Time hrs.[3] | H$_2$O distilled, % of theory | R$_2$O formed % |
|---|---|---|---|---|---|
| 1A* | Toluene-sulfonic Acid | 50 | 42 | 92 | Substantial |
| 1B* | Stannous Oxalate | 50 | 71 | 63 | Trace |

*Comparative Example
[1] 5 wt % on 3,5,6-trichlorosalicylic acid
[2] Mol % on 3,5,6-trichlorosalicylic acid
[3] Time to cessation of water distillation
[4] Tetraisopropyl titanate
[5] Tetra-n-butyl titanate
[6] Acetylacetonate titanate chelate
[7] Ethyl acetoacetate titanate chelate The foregoing data demonstrate that use of the titanium catalysts of Examples 2-5 according to this invention leads to high yields and rapid reaction times and low amounts of dipentyl ether byproduct. The acid catalyst, Comparative Example 1A*, provides slower reaction times and nearly as high yields, and undesirably substantial amounts of byproduct dipentyl ether. The tin catalyst sometimes used in the prior art, provides low amounts of by product ether, but an extremely long reaction time and low yield of water of reaction.

The following Example illustrates a procedure to make n-pentyl 3,5,6-trichlorosalicylate from salicylic acid using a titanium catalyst according to this invention instead of a sulfuric acid catalyst in the esterification step.

EXAMPLE 6

(A) Preparation of 3,5,6-trichlorosalicylic Acid

Sulfuric acid (96.0%; 505 parts) is charged into a suitable round bottomed vessel, equipped with a thermometer, stirrer, and sintered glass gas inlet tube, and cooled to 8°-10° C. Salicylic acid (115 parts; 0.83 mole) is added to the sulfuric acid and the mixture is stirred until the salicylic acid is completely dissolved. The resulting solution is cooled to 5° C. and chlorine gas is bubbled into it while maintaining the temperature at 5°-10° C. After about 45-50 minutes, 3,5-dichlorosalicylic acid starts to precipitate from solution. After chlorinating at 5°-10° C. for about 2 hours and 10 minutes beyond the onset of precipitation of 3,5-dichlorosalicylic acid, the reaction mixture is heated to 65°-70° C. and chlorination is continued for an additional 2 hours and 10 minutes at the elevated temperature. Chlorination is then discontinued, the reaction mixture is cooled to 10° C. and sulfur trioxide (4.53 moles) is carefully added thereto at a rate to keep the temperature at or below 55° C. Iodine (1 part) is added to the action mixture and chlorination is resumed with the temperature at 50° C. After chlorinating for 35 minutes, a tan solid precipitates and chlorine uptake ceases. Analysis of the reaction mixture at this point shows that it is about 96% completed. The addition of chlorine is continued and the reaction mixture is stirred at 50° C. for an additional hour. The reaction mixture is then poured on a mixture of 2800 parts of cracked ice and water affording a yellow precipitate of the desired product in a yield of 77.7% of theoretical.

(B) Preparation of n-Pentyl 3,5,6-Trichlorosalicylate

The mixture of cracked ice and yellow precipitate is extracted for one hour at 95° C. with 550 mls of a mixture of 1.75:1 parts by volume of xylene:n-pentanol. The mixture is allowed to settle. The organic layer is separated, and the aqueous layer is extracted again for one hour at 95° C. with 450 mls of xylene:n-pentanol mixture. Again the mixture is allowed to settle, the organic phase is separated and combined with the first organic extract and water is removed to less than 0.2 weight percent. The total extract is charged into a 2-liter round-bottomed flask equipped with a Dean-Stark trap and a condenser. To the contents is added tetraisopropyl titanate in an amount to provide 5 wt % based on the 3,5,6-trichlorosalicylic acid and the mixture is refluxed while separating water by means of the Dean-Stark trap until water ceases to come over, yielding the desired product.

EXAMPLE 7

Preparation of Methyl 3,5,6-trichlorosalicylate.

The procedure of Example 6, step (A) is repeated. The mixture of cracked ice and yellow precipitate, comprising 3,5,6-trichlorosalicylic acid, is extracted for one hour at 95° C. with 550 mls of xylene. The mixture is allowed to settle. The organic layer is separated, and the aqueous layer is extracted again for one hour at 95° C. with 450 mls of xylene. Again the mixture is allowed to settle, the organic phase is separated and combined with the first organic extract and water is removed to less than 0.2 weight percent. Methanol, 150 mol %, based on the 3,5,6-trichlorosalicylic acid then is added. The mixture is then charged into a suitable reaction vessel equipped with a Dean-Stark trap and a condenser. To the contents is added tetraisopropyl titanate in an amount to provide 5 wt % based on the 3,5,6-trichlorosalicylic acid and the mixture is refluxed while separating water by means of the Dean-Stark trap until water ceases to come over. The desired product is obtained in high yield.

EXAMPLE 8

Preparation of Octyl 3,5,6-trichlorosalicylate

The procedure of Example 1 is repeated substituting n-octanol for n-pentanol. The desired product is obtained in similar yields.

EXAMPLE 9

Preparation of Dodecyl 3,5,6-trichlorosalicylate

The procedure of Example 1 is repeated substituting n-dodecanol for n-pentanol. The desired product is obtained in similar yields.

EXAMPLE 10

Preparation of Octadecyl 3,5,6-trichlorosalicylate

The procedure of Example 1 is repeated substituting n-octadecanol for n-pentanol. The desired product is obtained in similar yields.

EXAMPLE 11

The procedure of Example 1 is again followed except that the solvent is dimethyl formamide. Similar results are obtained.

The patents, any publications, and the test methods mentioned above are incorporated herein by reference.

Many variations of the invention will suggest themselves to those skilled in this art in light of the above detailed description. All such obvious variations are within the full intended scope of the appended claims.

We claim:

1. A process for preparing esters of 3,5,6-trichlorosalicylic acid represented by the formula

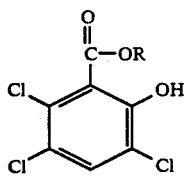

in which R represents alkyl ($C_1$–$C_{20}$) comprising:
(1) preparing a reaction mixture comprising 3,5,6-trichlorosalicylic acid, a solvent, and, from about 100 mol % to about 175 mol % based on said 3,5,6-trichlorosalicylic acid, of an alcohol having 1 to 20 carbon atoms,
(2) adding a catalytic amount of a tetraalkyl titanate or a titanium chelate to the mixture of step (1) and,
(4) heating the mixture and distilling until removal of water from the mixture is substantially complete, leaving a solution containing the compound of formula (I), trace amounts or less of by-product ether of the formula $R_2O$, wherein R is as above defined, and tolerable amounts of unreacted 3,5,6-trichlorosalicylic acid.

2. The process of claim 1 wherein the alcohol used for the esterification contains 2–8 carbon atoms and the initial reaction mixture contains about 150 mol % of said alcohol, based on said 3,5,6-trichlorosalicylic acid.

3. The process of claim 2 wherein said alcohol comprises n-pentanol.

4. The process of claim 1 wherein said tetraalkyl titanate or titanium chelate is present in an amount of from about 1.5 to about 7.5 wt %, based on said 3,5,6-trichlorosalicylic acid, and is selected from (i) those of the formula $(R'O)_4Ti$, wherein the groups R' represent independently an alkyl group of from 2 to 10 carbon atoms; (ii) an acetonyl acetonate chelate of titanium; (iii) an ethyl acetoacetate titanium chelate; or (iv) a mixture of any of the foregoing.

5. The process of claim 4 wherein the titanium compound comprises from about 2.0 to about 5.0 wt %, and is selected from tetraisopropyl titanate, tetra-n-butyl titanate, titanium acetonyl acetonate chelate, titanium ethyl acetoacetate chelate, or a mixture of any of the foregoing.

6. The process of claim 1 wherein the solvent comprises a mixture of xylene isomers, toluene or a mixture of any of them.

7. The process of claim 6 wherein the mixture prior to distillation comprises about 4.0–7.0 parts by weight of a mixture of (i) toluene and xylenes or (ii) xylenes and about one part by weight of n-pentanol and the n-pentanol is present in an amount corresponding to about 150 mol % based on said 3,5,6-trichlorosalicylic acid.

8. An improved process for preparing esters of 3,5,6-trichlorosalicylic acid represented by the formula

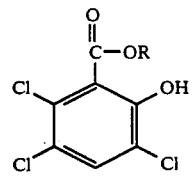

in which R represents alkyl ($C_1$–$C_{20}$) comprising:
(1) contacting a solution of salicylic acid in concentrated sulfuric acid with chlorine at a temperature below 35° C., until essentially all of the salicylic acid is converted into monochlorosalicylic acid, further converting the monochlorosalicylic acid to 3,5-dichlorosalicylic acid by contacting it with chlorine at a temperature in the range 50°–75° C.,
(2) adding to the product solution of 3,5-dichlorosalicylic acid about 4 moles of sulfur trioxide for each mole of salicylic acid that was used in step (1), with the temperature of the solution at or below 55° C., during the addition of sulfur trioxide,
(3) adding a catalytic amount of iodine to the solution obtained by step (2),
(4) contacting the solution obtained in step (3) with gaseous chlorine while maintaining the solution temperature about 40°–60° C., until absorption of chlorine by the solution has ceased,
(5) cooling the reaction mixture from step (4) to ambient temperature and adding the cooled reaction mixture to water at 0° C., thereby precipitating 3,5,6-trichlorosalicylic acid as a solid,
(6) extracting the water containing precipitated 3,5,6-trichlorosalicylic acid with a water-immiscible solvent at a temperature of at least 60° C. to form a two-phase liquid mixture with the 3,5,6-trichlorosalicylic acid in the organic phase,
(7) separating the organic phase from the aqueous phase,
(8) removing water from the organic phase, if necessary, to less than 0.2 weight percent,
(9) adding from about 100 mol % to about 175 mol %, based on said 3,5,6-trichlorosalicylic acid, of an alcohol having 1 to 20 carbon atoms,
(10) adding a catalytic amount of a tetraalkyl titanate or a titanium chelate to the separated organic phase, and,
(11) distilling the water azeotrope from the mixture leaving a solution containing the compound of formula (I), trace amounts or less of by-product ether of the formula $R_2O$, wherein R is as above defined, and tolerable amounts of unreacted 3,5,6-trichlorosalicylic acid.

9. The process of claim 8 wherein the gaseous chlorine is contacted with the solution of salicylic acid at a temperature of 5°–10° C., the 5-chlorosalicylic acid is converted to 3,5-dichlorosalicylic acid by contact with chlorine at 65°–70° C.; 100–150 milligrams of iodine per mole of the salicylic acid charged in step (1) is added in step (3), and gaseous chlorine is contacted with the reaction mixture at about 47°–54° C. in step (4).

10. The process of claim 8 wherein the alcohol used for the esterification contains 2–8 carbon atoms and the initial reaction mixture contains about 150 mol % of said alcohol, based on said 3,5,6-trichlorosalicylic acid.

11. The process of claim 10 wherein said alcohol comprises n-pentanol.

12. The process of claim 8 wherein said tetraalkyl titanate or titanium chelate is present in an amount of from about 1.5 to about 7.5 wt %, based on said 3,5,6-trichlorosalicylic acid, and is selected from (i) those of the formula $(R'O)_4Ti$, wherein the groups $R'$ represent independently an alkyl group of from 2 to 10 carbon atoms; (ii) an acetonyl acetonate chelate of titanium; (iii) an ethyl acetoacetate titanium chelate; or (iv) a mixture of any of the foregoing.

13. The process of claim 12 wherein the titanium compound comprises from about 2.0 to about 5.0 wt %, and is selected from tetraisopropyl titanate, tetra-n-butyl titanate, titanium acetonyl acetonate chelate, titanium ethyl acetoacetate chelate, or a mixture of any of the foregoing.

14. The process of claim 8 wherein the water-immiscible solvent comprises a mixture of xylene isomers, toluene or a mixture of any of them.

15. The process of claim 14 wherein the mixture prior to azeotropic distillation comprises about 4.0–7.0 parts by weight of a mixture of (i) toluene and xylenes or (ii) xylenes and about one part by weight of n-pentanol and the n-pentanol is present in an amount corresponding to about 150 mol % based on said 3,5,6-trichlorosalicylic acid.

16. The process of claim 1 wherein the solvent is water-immiscible.

17. The process of claim 1 wherein the distillation is azeotropic distillation.

* * * * *